(12) United States Patent
Denyer et al.

(10) Patent No.: US 8,371,299 B2
(45) Date of Patent: Feb. 12, 2013

(54) VENTILATOR AEROSOL DELIVERY

(75) Inventors: Jonathan S. H. Denyer, Chichester (GB); Ivan R. Prince, Chichester (GB)

(73) Assignee: Respironics Respiratory Drug Delivery, West Sussex (GB)

( * ) Notice: Subject to any disclaimer, the term of this patent is extended or adjusted under 35 U.S.C. 154(b) by 845 days.

(21) Appl. No.: 12/100,487

(22) Filed: Apr. 10, 2008

(65) Prior Publication Data

US 2008/0257337 A1 Oct. 23, 2008

Related U.S. Application Data

(60) Provisional application No. 60/925,308, filed on Apr. 19, 2007.

(51) Int. Cl.
*A62B 7/00* (2006.01)

(52) U.S. Cl. ......... 128/204.23; 128/200.14; 128/203.12; 128/204.18; 128/204.26

(58) Field of Classification Search ............. 128/203.12, 128/203.14, 204.18, 204.21, 204.23
See application file for complete search history.

(56) References Cited

U.S. PATENT DOCUMENTS

| | | | |
|---|---|---|---|
| 3,812,854 A | 5/1974 | Michaels et al. | |
| 3,921,637 A | 11/1975 | Bennie et al. | |
| 4,114,608 A | 9/1978 | Russo | |
| 4,268,460 A | 5/1981 | Boiarski et al. | |
| 4,986,269 A | 1/1991 | Hakkinen | |
| 5,063,922 A | 11/1991 | Hakkinen | |
| 5,277,175 A * | 1/1994 | Riggs et al. | 128/200.21 |
| 5,507,281 A | 4/1996 | Kuhnel et al. | |
| 5,713,349 A | 2/1998 | Keaney | |
| 5,918,596 A * | 7/1999 | Heinonen | 128/204.21 |
| 6,105,575 A | 8/2000 | Estes et al. | |
| 6,467,477 B1 | 10/2002 | Frank et al. | |
| 6,606,989 B1 | 8/2003 | Brand et al. | |
| 7,766,012 B2 * | 8/2010 | Scheuch et al. | 128/203.21 |
| 2003/0070681 A1 | 4/2003 | Rydgren | |
| 2005/0056283 A1 | 3/2005 | Levi et al. | |
| 2005/0284469 A1 | 12/2005 | Tobia et al. | |

FOREIGN PATENT DOCUMENTS

WO      WO 2004045690 A1 *   6/2004

* cited by examiner

*Primary Examiner* — Justine Yu
*Assistant Examiner* — LaToya M Louis
(74) *Attorney, Agent, or Firm* — Timothy A. Nathan

(57) ABSTRACT

The delivery of a medicament to a mechanically ventilated patient may include the steps of delivering a respiratory maneuver to such a patient, monitoring the physiological effects of the respiratory maneuver on such patient, automatically establishing an adjustment to the respiratory maneuver in response to the monitored physiological effects, and delivering the adjusted respiratory maneuver to such a patient.

21 Claims, 5 Drawing Sheets

FIG. 1

Patient Flow — Aerosol Pulse, "Clean-Air" Period, Respiratory Maneuver

FIG. 4

Lung Compliance

FIG. 5

Lung Resistance

FIG. 6

Circuit Pressure

FIG. 7

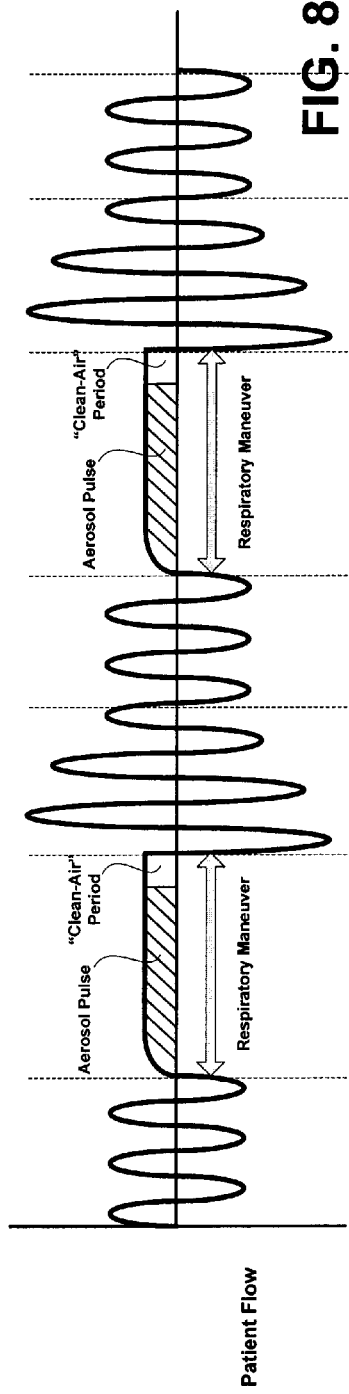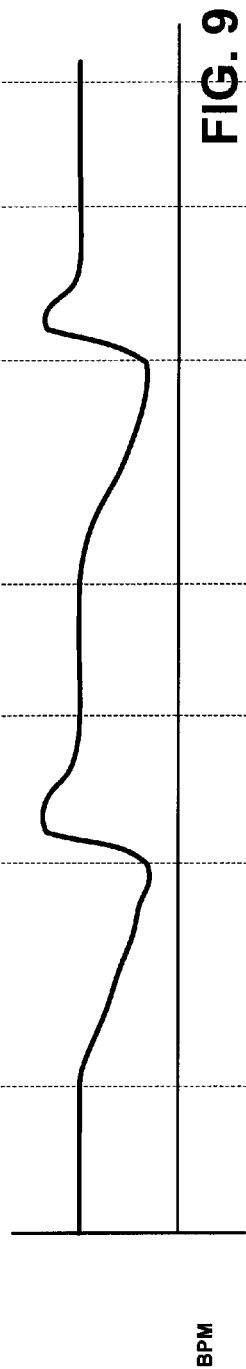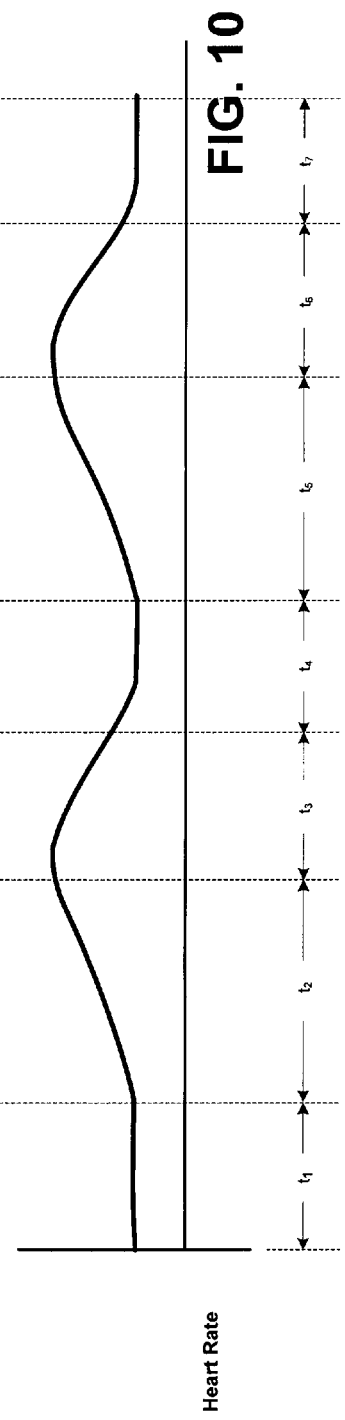

VENTILATOR AEROSOL DELIVERY

CROSS REFERENCE TO RELATED APPLICATIONS

This application claims priority under 35 U.S.C. §119(e) from provisional U.S. patent application No. 60/925,308 filed Apr. 19, 2007 the entire contents of which are incorporated herein by reference.

BACKGROUND OF THE INVENTION

1. Field of the Invention

The present invention pertains generally to administering an aerosolized medicament to a patient, and more particularly, to optimizing the delivery of a respiratory maneuver to increase the effectiveness of medicament delivery.

2. Description of the Related Art

It is known to deliver a medicament via a patient's respiratory tract. Such a delivery approach has allowed the development of therapeutic regimens for treating localized and systemic effects of diseases, especially diseases affecting the pulmonary system.

A nebulizer is a common device employed to deliver medicaments via the respiratory tract. Generally, a nebulizer converts an aqueous-based medicament into an aerosol which is inhaled by a patient. Nebulizers may employ different mechanisms for aerosolizing a medicament. For example, pneumatic (or jet) nebulizers employ compressed air to disperse the aqueous-based medicament into aerosol form. An ultrasonic nebulizer, in contrast, employs an electrical source to excite a piezoelectric element which generates high frequency vibrations. These vibrations cause small droplets to separate from the surface of the aqueous-based medicament, thus forming an aerosol. Vibrating mesh technology (VMT) nebulizers employ a mesh having a number of microscopic apertures therein. A vibration is induced in the mesh (or in another component within the nebulizer) which causes the aqueous-based medicament to be extruded through the mesh apertures. The aqueous-based medicament is ejected from the mesh apertures in aerosol form.

It is important that the dosage of medicament prescribed by a physician be administered in a reproducible and precise manner. Reproducibility and precision are greatly dependent upon one or more respiration maneuvers performed during administration of the medicament. The terms “respiration maneuver”, “maneuver”, and derivatives thereof refer to a number of respiratory cycle characteristics and/or dosing characteristics related to the administration of a partial and/or complete dose of a medicament. The term respiration maneuver may be understood to encompass, for example and without limitation, the number of breathes per minute (BPM), the inspiratory flow rate, the tidal volume, the volume of aerosol delivered to the patient, the aerosol pulse duration, and the duration of the dosing event.

U.S. patent application Ser. No. 10/535,597 to Denyer et al., which has the same inventorship and assignee as the instant application, the entire contents of which are incorporated herein, teaches a respiration maneuver which improves the precision and repeatability of medicament delivery to a patient. Generally, Denyer et al. teach a method of generating signals in a drug delivery apparatus through which a patient is receiving a dose of medicament. These signals may be used as feedback to aid the patient in completing a desired respiration maneuver. Denyer et al., however, is generally directed to patients capable of spontaneous breathing (e.g., non-ventilated patients). Mechanically ventilated patients, in contrast, may not be able to adequately respond to the generated feedback signals, and thus fail to complete the desired respiratory maneuver.

The delivery of an aerosolized medicament to a patient through a ventilator circuit can be inefficient. In some cases, only ten to thirty percent of the nominal dose actually reaches the patient. The remaining medicament may be, for instance, carried away in the exhalation stream or lost to impaction with the ventilator circuit, endotracheal tube, and the patient's upper airway.

Attempts made to reduce medicament lost in the exhalation stream include, for example, triggering the aerosol generator only during inhalation, increasing the sedimentation time, and orienting the patient's position during administration of the aerosolized medicament. Attempts made to reduce medicament loss due to impaction include, for example, relocating the aerosol generator (e.g., a nebulizer) between the ventilator circuit and patient interface device (e.g., endotracheal tube; mask; etc.), suspending humidification during aerosol generation, and reducing the inhalation flow rate. Each of these attempts produce less than desirable results and generally requires an affirmative act by the clinician. For example, a clinician must manually adjust the ventilator's settings to reduce the inhalation flow rate.

Accordingly, a need exists for an apparatus and method for providing improved delivery of an aerosolized medicament to a ventilated patient which overcomes these and other problems associated with known systems.

SUMMARY OF THE INVENTION

In accordance with an aspect of the present invention, a method for delivering a medicament to a mechanically ventilated patient receiving a flow of breathing gas comprises delivering a respiratory maneuver to such a patient, monitoring the physiological effects of the respiratory maneuver on such patient, automatically establishing an optimized respiratory maneuver in response to the monitored physiological effects, and delivering the optimized respiratory maneuver to such a patient.

According to another aspect of the present invention, a method for coordinating delivery of a flow of gas and delivery of a medicament to a mechanically ventilated patient comprises generating the flow of gas with a flow generator, determining a number of first operational parameters associated with the flow generator, establishing a respiratory maneuver, wherein the respiratory maneuver includes a number of second operational parameters associated with the flow generator and a number of operational parameters associated with a medicament delivery device, delivering the respiratory maneuver to such patient, wherein the number of second operational parameters associated with the flow generator and the number of operational parameters associated with the medicament delivery device are implemented in a coordinated fashion, monitoring such patient's physiological reaction to the respiratory maneuver, and automatically establishing an optimized respiratory maneuver responsive to such patient's physiological reaction.

According to another aspect of the present invention, a system for delivering an aerosolized medicament to a ventilated patient comprises a ventilator structured to produce a flow of breathing gas, a nebulizer structured to aerosolize a medicament, a monitoring device structured to generate an output signal associated with a response of such a patient to receipt of the aerosolized medicament, and a controller operatively coupled with the ventilator, nebulizer, and monitoring device, wherein the controller is adapted to coordinate operation of the ventilator and the nebulizer to produce a respiratory maneuver, and responsive to the output signal from the monitoring device, automatically establish ventilator settings and nebulizer settings to optimize delivery of the aerosolized medicament to such patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Figure 1:
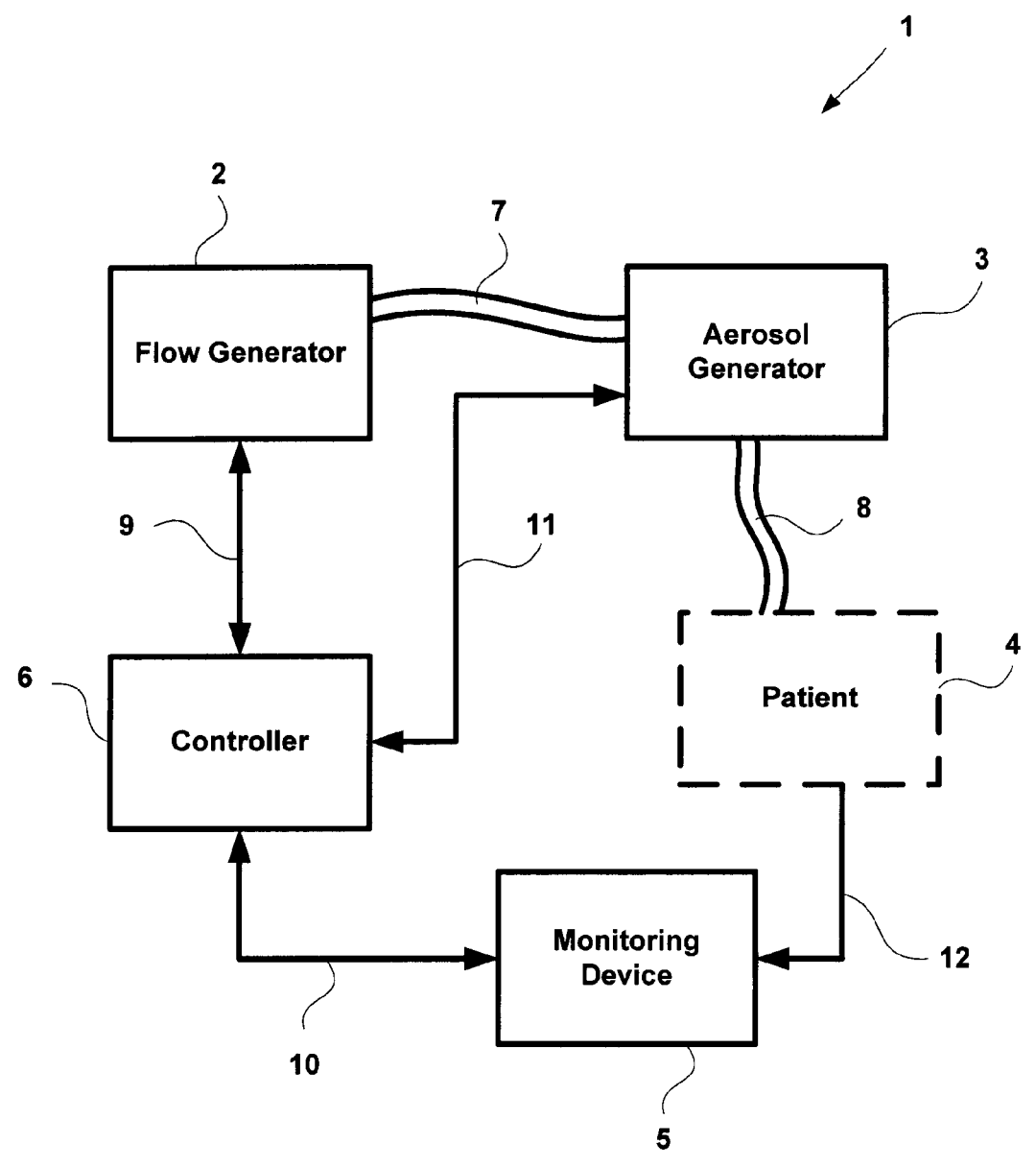

FIG. 1 is a schematic view of a system adapted to provide a regimen of respiratory therapy according to one embodiment of the present invention.

FIG. 2 illustrates an operational process for delivering a medicament to a mechanically ventilated patient according to one embodiment of the present invention.

FIG. 3 illustrates an operational process for delivering a medicament to a mechanically ventilated patient according to another embodiment of the present invention.

FIG. 4 is a graph illustrating delivery of an aerosolized medicament to a mechanically ventilated patient according to one embodiment of the present invention.

FIG. 5 is a graph illustrating lung compliance related to delivery of the aerosolized medicament of FIG. 4.

FIG. 6 is a graph illustrating lung resistance related to delivery of the aerosolized medicament of FIG. 4.

FIG. 7 is a graph illustrating circuit pressure related to delivery of the aerosolized medicament of FIG. 4.

FIG. 8 is a graph illustrating an aerosolized medicament treatment to a mechanically ventilated patient according to one embodiment of the present invention.

FIG. 9 is graph illustrating breathes per minute related to the aerosolized medicament treatment of FIG. 8.

FIG. 10 is graph illustrating heart rate related to the aerosolized medicament treatment of FIG. 8.

DETAILED DESCRIPTION OF THE EXEMPLARY EMBODIMENTS

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of"a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

A system 1 for delivering an aerosolized medicament to a ventilated patient according to one embodiment is shown in FIG. 1. System 1 includes a flow generator 2, an aerosol generator 3, a patient monitoring device 5, and a controller 6.

Flow generator 2 is structured to generate a flow of breathing gas which is communicated through a patient circuit 7 to a patient 4. In the current embodiment, a ventilator 2, such as a BiPap® Vision® ventilator or a BiPap® Focus® ventilator, each available from Respironics, Inc. of Murrysville, Pa., is employed as the flow generator, although it is contemplated that other devices may be used. As seen in FIG. 1, the flow of breathing gas is delivered to patient 4 via a patient interface device 8, such as an endotracheal tube 8, which is in fluid communication with patient circuit 7. It is contemplated that other patient interfaces may be employed. Aerosol generator 3 is located downstream of patient circuit 7; here between patient circuit 7 and endotracheal tube 8. As a result, impaction of aerosolized medicament within patient circuit 7 is eliminated. A nebulizer 3, such as a Sidestream® nebulizer available from Respironics, Inc., is employed as the aerosol generator in the current embodiment, although it is contemplated that other devices may be used.

Monitoring device 5 is structured to track a patient's 4 physiological state, for example, in response to a delivered respiratory maneuver. Examples of such a monitoring device 5 includes a NICO® Cardiopulmonary Management System and a Capnogard® Capnograph, each available from Respironics, Inc., although it is contemplated that other devices may be used. A number of sensors (not shown in FIG. 1) are typically applied to patient 4 and communicate with monitoring device 5 via signal line 12. Although illustrated as communicating via a hard-wired connection, it is contemplated that monitoring device 5 may wirelessly communicate with the number of sensors while remaining within the scope of the present invention. Monitoring device 5 may receive signals associated with, for example and without limitation, lung compliance, airway resistance, circuit pressure, respiratory rate, minute volume, partial pressure of oxygen in arterial blood, partial pressure of carbon dioxide in arterial blood, and percentage of oxygen saturation in arterial blood.

Controller 6 may include a processor, a memory, and a user interface device (not shown), among others. Generally, the processor is adapted to implement a number of routines for optimizing the delivery of a respiratory maneuver. The routines may be in any of a variety of forms such as, without limitation, software, firmware, and the like which are executable by the processor. For example, the processor may be adapted to implement a routine for coordinating the operations of ventilator 2 and nebulizer 3. The memory can be any of a variety of types of internal and/or external storage media such as, without limitation, RAM, ROM, EPROM(s), EEPROMS(s), and the like that provide a register for data storage such as in the fashion of an internal storage area of a computer, and can be volatile memory or nonvolatile memory. The memory provides storage for, among others, the number of routines executable by the processor. The user interface may include, without limitation, a mouse, a keyboard, and/or a display.

Controller 6 is structured to communicate with ventilator 2, nebulizer 3, and monitoring device 5. In the current embodiment, controller 6 communicates with ventilator 2 via signal line 9, with nebulizer 3 via signal line 11, and with monitoring device 5 via signal line 10. Although illustrated as communicating via hard-wired connections, it is contemplated that system 1 may incorporate one or more wireless communication devices (e.g., controller 6 may wirelessly communicate ventilator 2, nebulizer 3, and/or monitoring device 5), while remaining within the scope of the present invention.

Although shown as discrete components in FIG. 1, it is contemplated that one or more of the devices and/or their functions may be combined into a single device while remaining within the scope of the present invention. For example, the functions of controller 6 may be incorporated into and carried out by ventilator 2.

System 1 is adapted such that the operation of ventilator 2 and nebulizer 3 are synchronized. As will be discussed in more detail herein, controller 6 is adapted, without limitation, to determine the breathing cycle of patient 4, activate nebulizer 3 during a portion of the patient's breathing cycle, and control the operation of the ventilator 2 during aerosol delivery. Controller 6 is also adapted to optimize the operations of ventilator 2 and nebulizer 3 in response to a patient's physiological reaction to the respiratory maneuver and/or to the delivered medicament.

Figure 2:
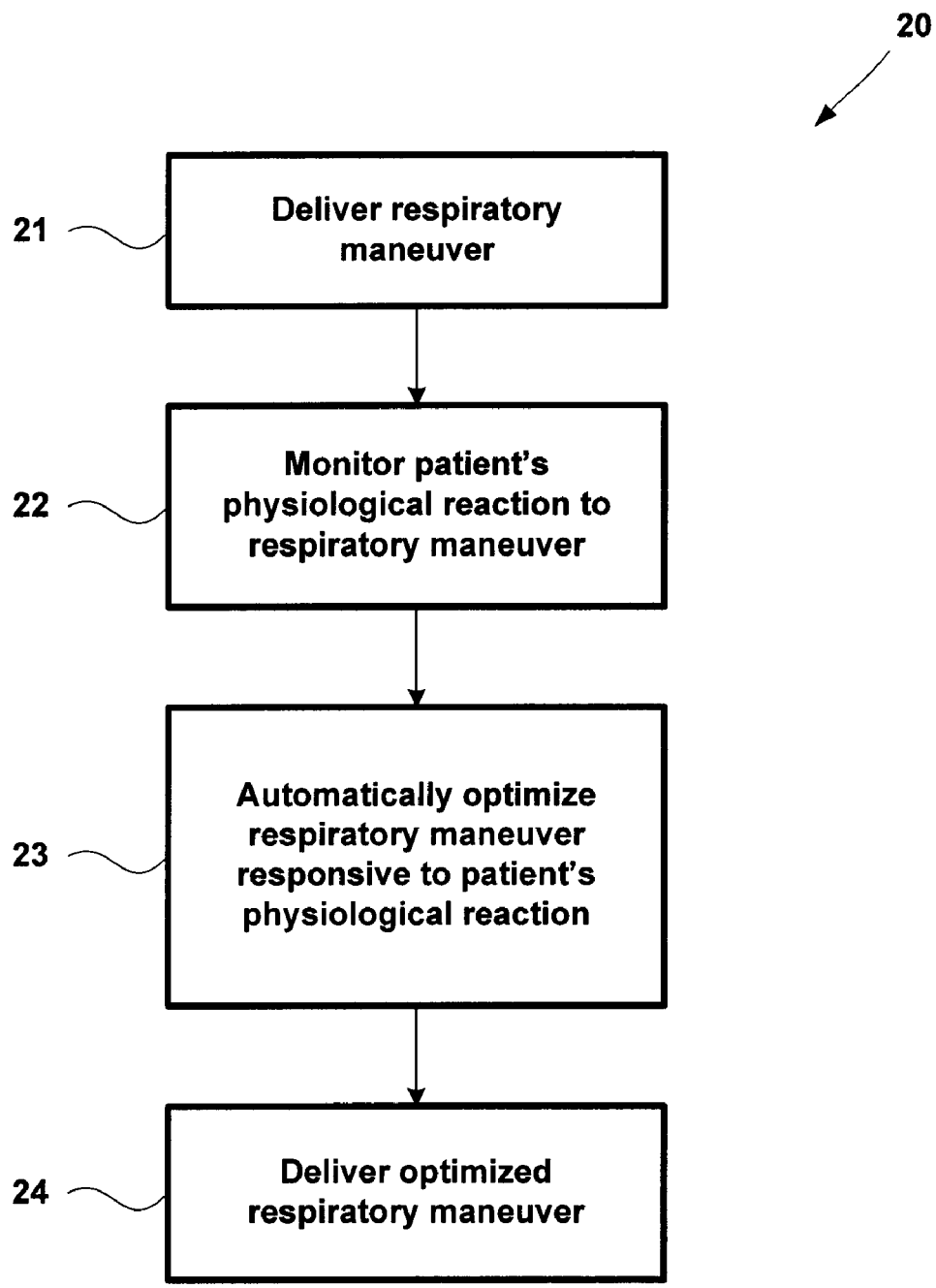

FIG. 2 illustrates an operational process for delivering a medicament to a mechanically ventilated patient according to one embodiment of the present invention. For example and without limitation, the patient in the current embodiment is a 154 pound (70 kg) average adult-sized male patient with a total lung capacity (TLC) of 6 liters (L), a vital capacity (VC) of 4.8 L, and a residual volume (RV) of 1.2 L. During normal breathing, it is assumed that such a patient has a tidal volume of five hundred milliliters (500 mL), a respiratory rate of ten breaths per minute (10 BPM), and a minute volume of five liters per minute (5 L/min). It should be apparent to one skilled in the art that the invention is in no way limited to such a patient and may easily be adapted for any patient.

At operation 21, a respiratory maneuver is delivered to such patient. In the current embodiment, controller 6 is adapted to synchronize the operation of the ventilator 2 and the nebulizer 3 such that a desired respiratory maneuver is produced. For example, controller 6 adjusts ventilator 2 to deliver a flow of breathing gas at a rate of twenty-four liters per minute (24 L/min) for a time period of approximately three seconds (3 sec). This maneuver provides a tidal volume of 1.2 L, which is approximately 25% of the patient's vital capacity. Additionally, controller 6 activates nebulizer 3 during the initial stages of the inhalation phase causing the medicament to be aerosolize and deactivates nebulizer 3 prior to the end of the inhalation phase (e.g., two seconds prior to the end of the inhalation stage) allowing a period of "clean air" to be delivered after the aerosol pulse.

At operation 22, the patient's physiological reaction to the respiratory maneuver and the delivered medicament is monitored. In the current embodiment, monitoring device 5 tracks the patient's physiological reaction to the respiratory maneuver and to the delivered medicament. A number of sensors (not shown in FIG. 1) are applied to the patient 4 and communicate with monitoring device 5 via signal line 12. Monitoring device 5 may receive signals associated with, for example and without limitation, lung compliance, airway resistance, circuit pressure, respiratory rate, minute volume, partial pressure of oxygen in arterial blood, partial pressure of carbon dioxide in arterial blood, and percentage of oxygen saturation in arterial blood.

At operation 23, the respiratory maneuver is automatically optimized in response to the patient's physiological reaction monitored in operation 22. In the current embodiment, monitoring device 5 communicates a number of signals associated with the patient's physiological reaction to controller 6 via signal line 10. Controller 6 employs these signals to calculate an optimized respiratory maneuver. For example, controller 6 may use signals associated with lung compliance, airway resistance, and circuit pressure to calculate a new inhaled volume that will be delivered by the optimized respiratory maneuver.

At operation 24, the optimized respiratory maneuver is delivered to the patient. In the current embodiment, controller 6 adjusts the settings of ventilator 2 and/or nebulizer 3 to deliver optimized respiratory maneuver. Controller 6 may adjust ventilator 2, for instance, to deliver a tidal volume of approximately 80% of the patient's vital capacity. For example, ventilator 2 is adjusted to deliver a flow rate of approximately fifty liters per minute (50 L/min) for a time period of approximately four-and-one-half seconds (4.5 sec.) and to activate nebulizer 3 during the initial stages of the inhalation phase and deactivate nebulizer 3 prior to the end of the inhalation phase (thus allowing a period of "clean air" to be delivered after the aerosol pulse).

It is contemplated that operations 22-24 may be repeated as many times necessary during the course of a treatment. For instance, multiple respiratory maneuvers may be required to deliver the entire prescribed dose of medicament during a single treatment (i.e., a treatment may consist of any number of respiratory maneuvers). Additionally, it is contemplated that the optimized maneuver settings associated with the last respiratory maneuver of a treatment may be used for the first respiratory maneuver of a subsequent treatment. As a result, aerosol delivery of the subsequent treatment is optimized (e.g., system 1 automatically "learns" patient's condition).

Figure 3:
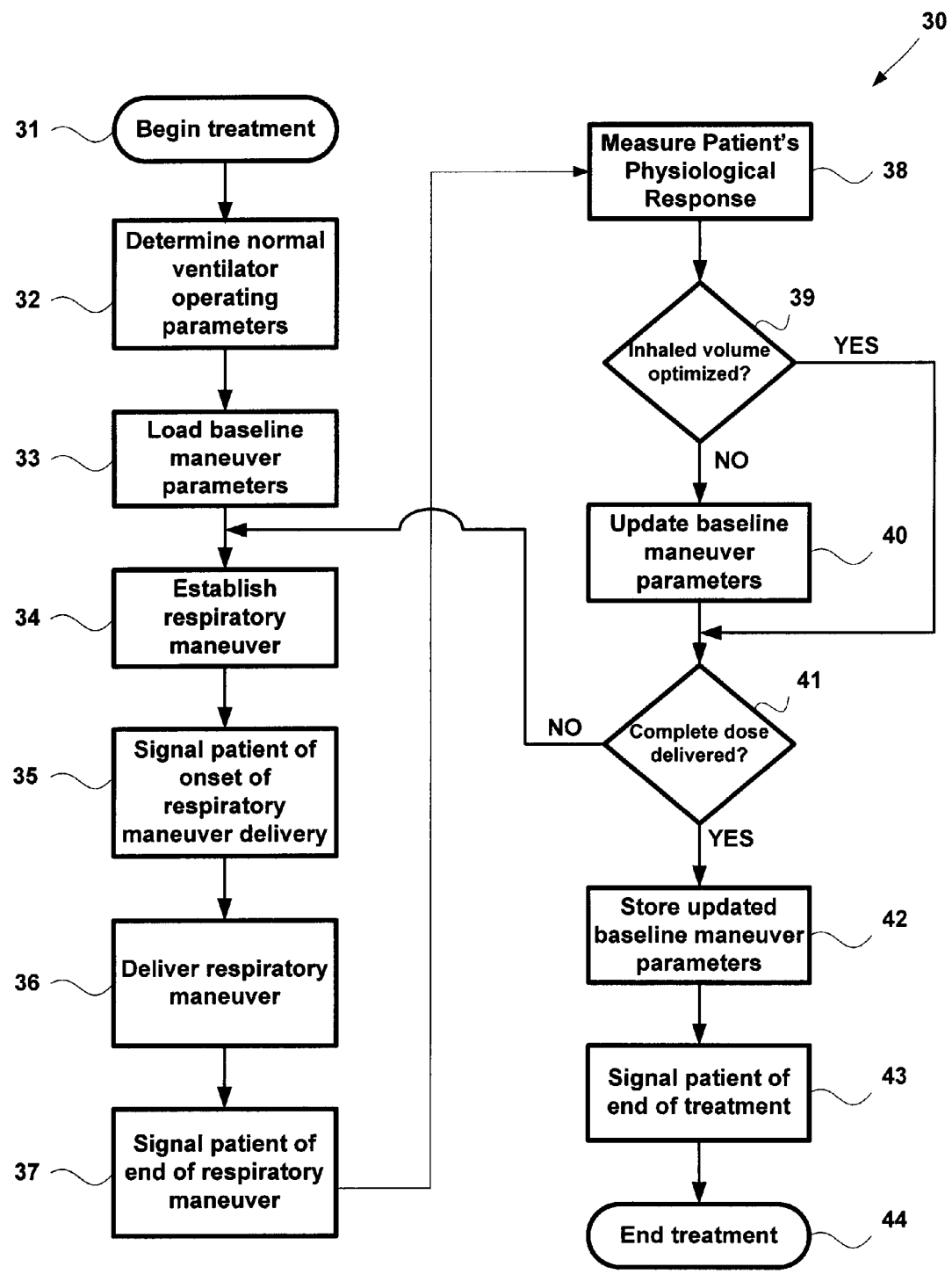

FIG. 3 illustrates an operational process 30 for delivering an aerosolized medicament according to another embodiment of the present invention. At operation 31 the treatment begins when a clinician loads a preset dose of aqueous-base medicament into the delivery system and designates the time period over which the medicament is to be delivered. In the current embodiment, for example, a clinician loads a preset dose of albuterol into nebulizer 3 and indicates that the dose is to be delivered over a period of 5 to 30 minutes.

Operational control then passes to operation 32 where the normal parameters of the ventilator are determined. In the current embodiment, controller 6 receives the normal parameters (e.g., the parameters associated with of a steady-state breathing cycle) from ventilator 2 via signal line 9. In the current embodiment, example, ventilator 2 is set to deliver a tidal volume of 500 mL at a flow rate of 25 L/min with an inhalation time of 1.2 seconds.

After receiving the normal parameters, operational control passes to operation 33 where the baseline respiratory maneuver parameters are loaded. In the current embodiment, the baseline respiratory maneuver parameters are derived from the normal ventilator settings and are loaded into controller 6. For example and without limitation, the tidal volume parameter for the baseline respiratory maneuver is 1.5 times the normal tidal volume parameter, the inhalation flow rate parameter for the baseline respiratory maneuver is 50% of the normal inhalation flow rate parameter, and an aerosol pulse time parameter for the baseline respiratory maneuver is approximately 25% of the normal inhalation time parameter and includes a maximum two-second "clean air" period.

After the baseline maneuver parameters are loaded, the respiratory maneuver is established in operation 34. In the current embodiment, controller 6 establishes the respiratory maneuver at this stage using the baseline maneuver parameters loaded in operation 33 and the normal operating parameters from operation 32. Continuing the above example, the tidal volume for the baseline respiratory maneuver is determined by the controller to be 750 mL (i.e., 1.5×500 mL), the inhalation flow rate is determined to be 12.5 L/min (i.e., 50% of 25 L/min), the inhalation time is determined to be 3.6 seconds, and a aerosol pulse time is determined to be 0.9 seconds (i.e., approximately 25% of 3.6 seconds.).

After the respiratory maneuver is established, operational control passes to operation 35 where a signal is generated informing the patient that the onset of the respiratory maneuver is approaching. In the current embodiment, for instance, an audible signal is generated. It is contemplated that any signal (such as without limitation, an audible signal, visual signal, and/or a tactile signal) or combination of signals may be used to inform the patient that the onset of the respiratory maneuver is approaching while remaining within the scope of the present invention.

After signal is generated in operation 35, operational control passes to operation 36 where the respiratory maneuver is delivered to the patient. In the current embodiment, controller 6 is adapted to deliver the respiratory maneuver established in operation 34. Accordingly, controller 6 sends a trigger signal and a flow time signal to ventilator 2 via signal line 9. In response, ventilator 2 reduces the inhalation flow rate from 25 L/min to 12.5 L/min and increases the tidal volume from 500 mL to 750 mL. Additionally, controller 6 sends an aerosol trigger signal to nebulizer 3 via signal line 11. In response, nebulizer 3 aerosolizes the aqueous-base medicament for 0.9 seconds (i.e., the aerosol pulse time). The aerosolized medicament is transported by the flow of breathing gas generated by ventilator 2 to the patient's lungs via endotracheal tube 8 and the patient's upper airway. Nebulizer 3 is deactivated prior to the end of the inhalation phase to provide a "clean air" period.

It is contemplated that controller 6 may issue other commands prior to, or subsequent to, delivery of the respiratory maneuver. Controller 6, for example, may issue a first command suspending the ventilator's humidifier operation prior to delivery of the respiratory maneuver and a second command reinstating humidifier operation subsequent to delivery of the respiratory maneuver.

After the respiratory maneuver is delivered, operational control passes to operation 37 where a signal is generated to inform the patient that the current respiratory maneuver has ended. In the current embodiment, for instance, an audible signal is generated. It is contemplated that any signal (such as without limitation, an audible signal, visual signal, and/or a tactile signal) or combination of signals may be used to inform the patient that the respiratory maneuver has ended while remaining within the scope of the present invention.

Next, operational control passes to operation 38 where the patient's response to the respiratory maneuver, and to the delivered medicament, is measured. In the current embodiment, ventilator 2 is employed to monitor several parameters such as, without limitation, lung compliance, airway resistance, and circuit pressure. These parameters are communicated to controller 6 via signal line 9. Additionally, monitoring device 5 is adapted to monitor several parameters such as, without limitation, breathes per minute (BPM), minute volume, saturation of oxygen ($S_AO_2$), carbon dioxide ($CO_2$), and heart rate. These parameters are communicated from monitoring device 5 to controller 6 via signal line 10.

After the patient's response is measured, a determination is made at operation 39 as to whether the inhaled volume is optimized. In the current embodiment, a tidal volume that is 80% of the patient's vital capacity is selected as a target and lung compliance, airway resistance, and circuit pressure parameters, among others, are used to determine if the inhalation volume for the next maneuver should be increased/decreased. Additionally, the BPM, minute volume, $S_AO_2$, $CO_2$, and heart rate parameters are used to determine whether adjustments can be made to the parameters of the next respiratory maneuver to minimize patient stress. It is contemplated that a metric other than or in addition to the tidal volume that is 80% of the patient's vital capacity may be employed to determine whether the respiratory maneuver is optimized.

If the inhaled volume is not optimized (e.g., in the current example, if the tidal volume setting of the respiratory maneuver is not 80% of the patient's vital capacity), operation 39 branches NO and operational control passes to operation 40 where the baseline maneuver parameters are updated. In the current embodiment, one or more of the baseline maneuver parameters are replaced by the respiratory parameters established in operation 34. After the baseline maneuver parameters are updated at operation 40, or if operation 39 branches YES, operational control passes to operation 41.

At operation 41, a determination is made as to whether the complete dose of aqueous-base medicament which was loaded into the delivery system by the clinician at operation 31 has been delivered. If a portion of the medicament remains, operation 41 branches NO and operational control returns to operation 34. At operation 34, the respiratory maneuver is established. It should be noted that this respiratory maneuver will include the updated baseline parameters, if any, from operation 40. Operations 34 through 41 are repeated until the complete dose of medicament is delivered to the patient and/or the time period over which the medicament is to be delivered (as designated in operation 31) expires. In the current embodiment, the time period between deliveries of respiratory maneuvers depends upon the patient's response to the previous respiratory maneuver. For instance, the first respiratory maneuver may have caused the patient's heart rate to increase. A subsequent respiratory maneuver will not be delivered until the patient's heart rate returns to an acceptable level.

If it is determined at operation 41 that the complete dose of aqueous-based medicament that was loaded into the nebulizer 3 has been delivered, operation 41 branches YES and operational control is passed to operation 42. At operation 42 the latest set of updated baseline parameters (as determined at operation 40), are stored. Accordingly, medicament delivery for subsequent treatments (e.g., the next time operational process 30 is implemented) will be optimized.

After the updated default settings are stored, operational control passes to operation 43 where a signal is generated indicating that current treatment has been completed. In the current embodiment, for instance, an audible signal is generated. It is contemplated that any signal (such as without limitation, an audible signal, visual signal, and/or a tactile signal) or combination of signals may be used to indicate that the current treatment has been completed while remaining within the scope of the present invention. It is preferable (though not necessary) that the signals generated in operation 35 (the signal informing the patient of the onset of the respiratory maneuver), operation 37 (the signal informing the patient of the end of the respiratory maneuver), and operation 43 (the signal informing the patient of the end of the current treatment) are sufficiently different so as not to confuse the patient as to the meaning of the generated signal.

After the signal indicating that the treatment has been completed is generated, operation 44 terminates operational process 30. In the current embodiment, controller 6 communicates to ventilator 2 that the treatment is completed. As a result, the parameters associated with of the patient's steady-state breathing cycle are loaded into ventilator 2. For instance, in the current example, ventilator 2 is reset to deliver a tidal volume of 500 mL at a flow rate of 25 liters per minute (L/min) at an inhalation time of 1.2 seconds. It is contemplated that these parameters may be updated as necessary to reflect any change in the patient's condition resulting from the treatment administration. For example, the effects of the administered medicament on the patient may necessitate that the tidal volume parameter be increase to 600 mL.

FIG. 4 is a graphical illustration of a single respiratory maneuver for the delivery of an aerosolized medicament to a mechanically ventilated patient according to one embodiment of the present invention. As seen in FIG. 4, the respiratory maneuver is applied during the inspiratory phase. The respiratory maneuver includes an aerosol pulse followed by a "clean-air" period, which immediately precedes the expiratory phase. FIGS. 5-7 illustrate lung compliance, lung resistance, and circuit pressure related to delivery of the aerosolized medicament shown in FIG. 4. Referring to FIG. 5, it can be seen that the amount of lung compliance generally decreases over the inhalation time period. In contrast, referring to FIGS. 6 and 7, it can be seen that lung resistance and circuit pressure remain relatively constant for the first portion of the inhalation phase, but then increase rapidly near the termination of the inhalation phase.

FIG. 8 illustrates the flow of breathing gas delivered to a mechanically ventilated patient during an aerosolized medicament treatment according to one embodiment of the present invention. FIGS. 9 and 10 illustrate breathes per minute BPM and heart rate, respectively, of such a patient in response to the aerosolized medicament treatment of FIG. 8.

During time period "$t_1$", a steady-state flow of breathing gas is delivered to a patient to maintain normal breathing. The patient's BPM and heart rate remain substantially constant.

During time period "$t_2$", a respiratory maneuver is delivered to the patient. As seen in FIG. 8, the respiratory maneuver includes a decrease in the normal (i.e., steady-state) flow rate, an increase in the normal (i.e., steady-state) tidal volume, and an aerosol pulse with a "clean-air" period. In response to the respiratory maneuver, the patient's BPM decreases and the patient's heart rate increases. The normal tidal volume and the normal flow rate associated with flow of gas are decreased for a first predetermined period and the nebulizer is activated for a second predetermined period which has a duration that is less than the duration of the first predetermined period. In the current embodiment, the duration of the second predetermined period (i.e., the duration of the aerosol pulse) is less than the duration of the first predetermined period (i.e., the duration of the entire respiratory maneuver) by the duration of the "clean-air" period.

After the respiratory maneuver is delivered, the amount of breathing gas delivered to the patient is somewhat transient. As seen in FIG. 8, a larger flow of breathing gas is delivered to the patient at the beginning of time period "$t_3$". In response, the patient's BPM increases and the patient's heart rate decreases. During time period "$t_3$", the amount of breathing gas delivered to the patient slowly settles until a steady-state is reached. In response, the patient's BPM and heart decrease return to a substantially constant level.

After the patient's BPM and heart rate have returned to a constant level (as shown at time period "$t_4$"), another respiratory maneuver is delivered during time period "$t_5$". In the current embodiment, this respiratory maneuver is optimized and may includes a decrease in the flow rate, an increase in the tidal volume, and an aerosol pulse with a "clean-air" period which may be different than that of the respiratory maneuver delivered during time period "$t_2$". In response to the respiratory maneuver delivered during time period "$t_5$", the patient's BPM decreases and the patient's heart rate increases.

After the respiratory maneuver is delivered, the amount of breathing gas delivered to the patient is somewhat transient. A larger flow of breathing gas is delivered to the patient at the beginning of time period "$t_6$". In response, the patient's BPM increases and the patient's heart rate decreases. During time period "$t_6$", the amount of breathing gas delivered to the patient slowly settles until a steady-state is reached. In response, the patient's BPM and heart decrease return to a substantially constant level (as shown during time period "$t_7$".

Although FIGS. 8-10 only illustrate the delivery of two respiratory maneuvers, it is contemplated that any number of respiratory maneuvers may be delivered to the patient while remaining within the scope of the present invention.

While specific respiratory maneuvers were employed to illustrate the disclosed embodiments, it should be apparent to one skilled in the art that the specific respiratory maneuver selected for administration to a patient may encompass a vast range of values. For example, it is contemplated that any number of respiratory maneuvers may be selected in which a tidal volume between 0-4000 milliliters, at a flow rate between 0-99 liters per minute, at an inhalation time between 0-10 seconds are delivered. Generally, it is contemplated that a selected respiratory maneuver will be selected in which a tidal volume between 100-1000 milliliters, at a flow rate between 10-50 liters per minute, at an inhalation time between 0.5 and 5 seconds is delivered.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A method for delivering a medicament during a single treatment session to a mechanically ventilated patient receiving a flow of breathing gas, the method being implemented in a respiratory therapy system, the method comprising:

delivering a first respiratory maneuver to a patient during a single treatment session, wherein the single treatment session comprises multiple deliveries of respiratory maneuvers to the patient, wherein the first respiratory maneuver includes:

(i) performing a temporary adjustment of a ventilation parameter pertaining to the flow of breathing gas for the patient, wherein the temporary adjustment is applied during a first time period within the first respiratory maneuver during the single treatment session, and wherein the temporary adjustment alters the flow of breathing gas delivered to the patient;

(ii) activating a drug delivery device structured to aerosolize the medicament during a second time period within the first respiratory maneuver during the single treatment session, wherein the second time period overlaps with the first time period and has a duration that is less than a duration of the first time period; and (iii) delivering the aerosolized medicament to the patient via the flow of gas;

measuring signals corresponding to physiological effects of the first respiratory maneuver on the patient, wherein the signals are measured during the single treatment session;

determining a modification of the temporary adjustment of the ventilation parameter for a second respiratory maneuver included in the single treatment session, wherein the modification is determined based on the measured signals corresponding to the physiological effects of the first respiratory maneuver; and delivering the second respiratory maneuver of the single treatment session to the patient using the modified temporary adjustment of the ventilation parameter, wherein the single treatment session further comprises a designated time period and a prescribed dose of medicament, wherein the prescribed dose of medicament is designated to be delivered during the designated time period using the multiple deliveries of respiratory maneuvers, and wherein the designated time period ranges from 5 to 30 minutes.

2. The method of claim 1, wherein determining the modification of the temporary adjustment of the ventilation parameter further includes determining the first time period and the second time period of the second respiratory maneuver.

3. The method of claim 1, wherein the ventilation parameter is a normal tidal volume, wherein the temporary adjustment of the normal tidal volume comprises increasing the normal tidal volume during the first respiratory maneuver, and wherein the modification of the temporary adjustment of the normal tidal volume used during the second respiratory maneuver comprises a modified normal tidal volume that is different than the increased normal tidal volume during the first respiratory maneuver.

4. The method of claim 1, wherein the ventilation parameter is a normal flow rate, wherein the temporary adjustment of the normal flow rate comprises decreasing the normal flow rate during the first respiratory maneuver, and wherein the modification of the temporary adjustment of the normal tidal volume used during the second respiratory maneuver comprises a modified normal tidal volume that is different than the decreased normal tidal volume during the first respiratory maneuver.

5. The method of claim 1, wherein a separating time period separates delivery of the first respiratory maneuver from delivery of the second respiratory maneuver, and wherein a length of the separating time period is based on the measured signals corresponding to physiological effects of the patient.

6. The method of claim 1, wherein determining the modification comprises at least two of:
   selecting a target tidal volume associated with the flow of gas during the second respiratory maneuver of the single treatment session;
   selecting a target flow rate associated with the flow of gas during the second respiratory maneuver of the single treatment session;
   selecting a target duration for the first time period of the second respiratory maneuver of the single treatment session; and
   selecting a target duration for the second time period of the second respiratory maneuver of the single treatment session.

7. The method of claim 1, wherein measuring of the signals corresponding to the physiological effects of the first respiratory maneuver on the patient includes measuring of at least one of lung compliance, airway resistance, circuit pressure, respiratory rate, minute volume, partial pressure of oxygen in arterial blood, partial pressure of carbon dioxide in arterial blood, and percentage of oxygen saturation in arterial blood.

8. The method of claim 1, further comprising generating an indication to the patient prior to delivery of the first respiratory maneuver and the second respiratory maneuver.

9. The method of claim 1, wherein delivering the first respiratory maneuver comprises delivering a tidal volume between 0-4000 milliliters at a flow rate between 0-99 liters per minute, at an inhalation time between 0-10 seconds.

10. The method of claim 1, wherein delivering the first respiratory maneuver comprises delivering a tidal volume between 100-1000 milliliters at a flow rate between 10-50 liters per minute, at an inhalation time between 0.5 and 5 seconds.

11. A method for coordinating delivery of a flow of gas and delivery of a medicament during a single treatment session to a mechanically ventilated patient, the method being implemented in a respiratory therapy system, the method comprising:
   generating the flow of gas with a flow generator;
   determining a first operational parameter associated with the flow generator, wherein the first operational parameter includes a normal tidal volume or a normal flow rate;
   establishing a first respiratory maneuver during a single treatment session, wherein the single treatment session comprises multiple deliveries of respiratory maneuvers to the patient, wherein the first respiratory maneuver includes:
   (i) a temporary adjustment of the first operational parameter associated with the flow generator, and
   (ii) delivery of a first dose of the medicament using a number of operational parameters associated with a medicament delivery device;
   delivering the first respiratory maneuver to the patient, wherein the temporary adjustment and the delivery of the first dose of the medicament are implemented in a coordinated fashion during the single treatment session;
   measuring the patient's physiological effects in response to the first respiratory maneuver, wherein the patient's physiological effects are measured during the single treatment session;
   determining a modification of the temporary adjustment of the first operational parameter for a second respiratory maneuver included in the single treatment session, wherein the second respiratory maneuver includes delivery of a second dose of the medicament, wherein the modification of the temporary adjustment of the first operational parameter is determined based on the measured patient's physiological effects; and
   delivering the second respiratory maneuver of the single treatment session, wherein the second respiratory maneuver includes the second dose of medicament, and wherein the second respiratory maneuver includes the modified temporary adjustment of the first operational parameter, wherein the single treatment session further comprises a designated time period and a prescribed dose of medicament, wherein the prescribed dose of medicament is designated to be delivered during the designated time period using the multiple deliveries of respiratory maneuvers, and wherein the designated time period ranges from 5 to 30 minutes.

12. The method of claim 11, wherein the first respiratory maneuver spans a first time period, wherein delivery of the medicament includes activation of a drug delivery device structured to aerosolize the medicament during a second time period within the first respiratory maneuver during the single treatment session, wherein the second time period overlaps with the first time period, and wherein the second time period has a duration that is less than a duration of the first time period.

13. The method of claim 12, wherein a separating time period separates delivery of the first respiratory maneuver from delivery of the second respiratory maneuver, and wherein a length of the separating time period is based on the measured patient's physiological effects.

14. The method of claim 12, wherein determining the modification of the temporary adjustment of the first operational parameter comprises at least two of:

selecting a target tidal volume associated with the flow of gas during the second respiratory maneuver of the single treatment session;

selecting a target flow rate associated with the flow of gas during the second respiratory maneuver of the single treatment session;

selecting a target duration for the first time period of the second respiratory maneuver of the single treatment session; and selecting a target duration for the second time period of the second respiratory maneuver of the single treatment session.

15. The method of claim 11, wherein the first operational parameter is a normal tidal volume, and wherein the temporary adjustment of the first operational parameter associated with the flow generator includes increasing the normal tidal volume.

16. The method of claim 11, wherein the first operational parameter is a normal flow rate, and wherein the temporary adjustment of the first operational parameter associated with the flow generator includes decreasing the normal flow rate.

17. The method of claim 11, wherein measuring the patient's physiological effects in response to the first respiratory maneuver includes measuring at least one of lung compliance, airway resistance, circuit pressure, respiratory rate, minute volume, partial pressure of oxygen in arterial blood, partial pressure of carbon dioxide in arterial blood, and percentage of oxygen saturation in arterial blood.

18. The method of claim 11, further comprising, generating an indication to the patient prior to the delivery of the first respiratory maneuver and the second respiratory maneuver.

19. The method of claim 11, wherein delivering the first respiratory maneuver comprises delivering a tidal volume between 0-4000 milliliters at a flow rate between 0-99 liters per minute, at an inhalation time between 0-10 seconds.

20. The method of claim 11, wherein delivering the first respiratory maneuver comprises delivering a tidal volume between 100-1000 milliliters at a flow rate between 10-50 liters per minute, at an inhalation time between 0.5 and 5 seconds.

21. A system for delivering an aerosolized medicament during a single treatment session to a ventilated patient, the system being implemented in a respiratory therapy system, the system comprising:

a ventilator structured to produce a flow of breathing gas corresponding to a ventilation parameter, wherein the ventilation parameter includes a normal tidal volume or a normal flow rate;

a nebulizer structured to aerosolize a medicament;

a monitoring device structured to generate one or more output signals associated with a measurement of a physiological response of the patient to receipt of the aerosolized medicament; and a controller operatively coupled with the ventilator, nebulizer, and monitoring device, wherein the controller is adapted to:

(i) coordinate a temporary adjustment of the ventilation parameter and operation of the nebulizer to deliver a first respiratory maneuver during a single treatment session, wherein the single treatment session comprises multiple deliveries of respiratory maneuvers to the patient, wherein the first respiratory maneuver includes delivery of a first dose of aerosolized medicament, wherein the temporary adjustment is applied during a first time period within the first respiratory maneuver during the single treatment session, (ii) responsive to the one or more output signals from the monitoring device, determine a modification of the temporary adjustment of the ventilation parameter for a second respiratory maneuver included in the single treatment session, and (iii) deliver the second respiratory maneuver that includes delivery of a second dose of aerosolized medicament in accordance with the modified temporary adjustment of the ventilation parameter, wherein the second respiratory maneuver is delivered during the single treatment session, wherein the single treatment session further comprises a designated time period and a prescribed dose of medicament, wherein the prescribed dose of medicament is designated to be delivered during the designated time period using the multiple deliveries of respiratory maneuvers, and wherein the designated time period ranges from 5 to 30 minutes.

* * * * *